United States Patent [19]

Darkes et al.

[11] 4,267,388

[45] May 12, 1981

[54] PROCESS FOR PRODUCING ETHYNYLBENZENES

[75] Inventors: Paul R. Darkes, Norristown; Henry F. Campbell, Lansdale; George H. Douglas, Malvern, all of Pa.

[73] Assignee: William H. Rorer, Inc., Fort Washington, Pa.

[21] Appl. No.: 56,984

[22] Filed: Jul. 12, 1979

[30] Foreign Application Priority Data

Jul. 13, 1978 [CA] Canada ................................. 307302

[51] Int. Cl.³ .................... C07C 41/18; C07C 41/24; C07C 25/18; C07C 25/24
[52] U.S. Cl. ............................ 568/642; 260/456 P; 585/400; 260/456 R; 424/340; 424/356; 424/353; 568/323; 568/316; 568/807; 570/193
[58] Field of Search ........ 260/651 R, 649 R, 649 DP; 568/642; 585/400

[56] References Cited

U.S. PATENT DOCUMENTS

| | | | |
|---|---|---|---|
| 2,060,303 | 11/1936 | Groll et al. ................... | 260/651 R X |
| 3,435,075 | 3/1969 | Glamkowski et al. ....... | 260/651 R X |
| 3,981,932 | 9/1976 | Diamond ...................... | 260/651 R X |
| 4,016,214 | 4/1977 | Douglas et al. .............. | 260/651 R X |
| 4,094,995 | 6/1978 | Diamond ...................... | 260/651 R X |

*Primary Examiner*—Bernard Helfin
*Attorney, Agent, or Firm*—Austin R. Miller; John Lezdey; James A. Nicholson

[57] ABSTRACT

There is disclosed a novel process for preparing anti-inflammatory ethynylbenzene derivatives represented by the general formula I:

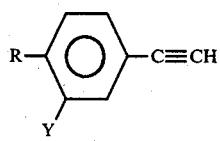

I wherein Y is hydrogen, halogen or loweralkyl of 1 to 3 carbon atoms; R represents a ring having the structure:

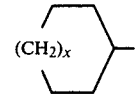

wherein x is 1 to 3, or a ring of the structure:

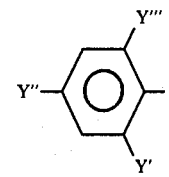

wherein Y' is hydrogen, halogen, loweralkyl of 1 to 3 carbon atoms and loweralkoxy of 1 to 3 carbon atoms; Y" is hydrogen or halogen; and Y'" is hydrogen or halogen, provided Y, Y', Y" and Y'" are not all hydrogen at the same time, by reacting a benzyl alcohol of formula V:

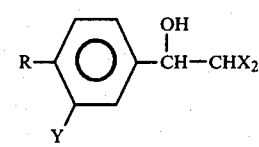

V with a sulfonyl chloride, reducing the sulfonate VI of the formula:

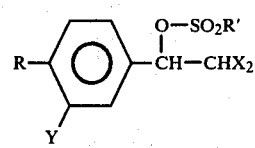

VI and dehydrohalogenating the formed β-halostyrene of the formula VII:

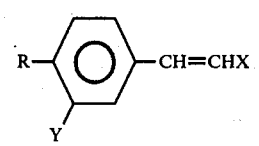

VII

12 Claims, No Drawings

PROCESS FOR PRODUCING ETHYNYLBENZENES

The present invention relates to a novel process for preparing ethynylbenzene derivatives represented by the general formula I:

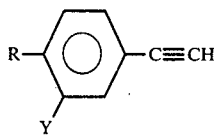

wherein:
Y is hydrogen, halogen or loweralkyl of 1 to 3 carbon atoms;
R represents a ring having the structure:

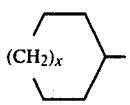

wherein x is 1 to 3 or

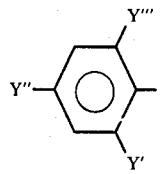

wherein
Y' is hydrogen, halogen, loweralkyl of 1 to 3 carbon atoms and loweralkoxy of 1 to 3 carbon atoms;
Y" is hydrogen or halogen; and
Y'" is hydrogen or halogen,
provided Y, Y', Y" and Y'" are not all hydrogen at the same time.

The compounds of formula I are known to possess antiinflammatory properties and manifest desirable analgesic and anti-pyretic properties.

The process of the present invention for preparing the compounds of formula I comprises the following steps:

In accordance with the present invention, a benzyl alcohol V of the general formula:

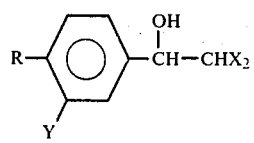

where X is chloro or bromo, is reacted with a sulfonyl chloride of the formula R'Cl, wherein R' is an alkyl, aryl or aralkylsulfonyl group, such as, for example, methanesulfonyl chloride, benzenesulfonyl chloride, p-toluenesulfonyl chloride, or the like, in the presence of a tertiary amine base to form the corresponding sulfonate VI of the formula:

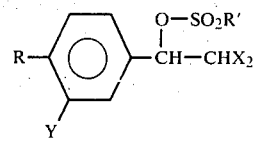

Reduction of the sulfonate VI in the presence of zinc or zinc and ammonium chloride provides the β-halostyrene VII of the formula:

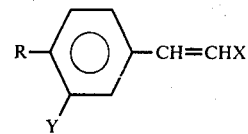

Finally, dehydrohalogenation of the β-halostyrene with strong base such as an alkali metal alkoxide, for example, potassium t-butoxide yields the desired ethynylbenzene derivative of formula I.

Reaction of the benzyl alcohol V with the sulfonyl chloride is carried out in the presence of a tertiary amine base such as pyridine, triethylamine, or the like, in an inert solvent such as methylene chloride.

The starting benzene alcohol of formula II may be obtained from a substituted acetophenone as described in U.S. Pat. No. 3,952,067, dated Apr. 20, 1976, which is incorporated herein by reference.

The final products obtained by the process of the present invention are also disclosed and claimed in Belgian Pat. No. 809,147 as useful as anti-inflammatory agents, and also, these products manifest desirable analgesic and anti-pyretic properties.

The instant process eliminates the use of costly reactants, equipment and labor.

The invention will be more readily understood by referring to the following examples which are provided to illustrate the invention rather than to limit its scope.

EXAMPLE 1

Synthesis of 3-Chloro-4-cyclohexyl-1-ethynylbenzene

STEP 1. Preparation of 4-Cyclohexylacetophenone

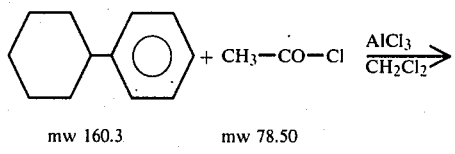

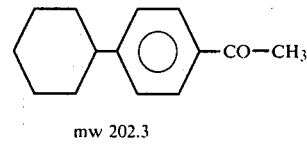

Into a 5 liter round bottom flask equipped with a mechanical stirrer was placed methylene chloride (2 l) and anhydrous aluminum chloride (485 g., 3.64 moles). The mixture was cooled below 5° C. in an ice bath and acetyl chloride (286 g., 3.64 moles) was added, with stirring and cooling, over 35 minutes during which time the temperature rose to 9° C. When the temperature had dropped to 3° C., cyclohexylbenzene 500 g., 3.12 moles) was added slowly with vigorous stirring, maintaining the temperature below 5° C. The addition required 3.5 hours, after which time stirring and cooling were continued for 1 hour. The mixture was then poured into ice (4000 g.) and concentrated hydrochloric acid (800 mls) and stirred for 1 hour. The layers were separated, and the aqueous phase was washed with a further portion (500 mls.) of methylene chloride. The combined methylene chloride extracts were concentrated to 1 liter, diluted with ether (2 ls) and washed 3 times with 10% aqueous hydrochloric acid (300 mls), and 3 times with water (300 mls. each). The ethereal extract was dried over sodium sulfate, filtered and evaporated to a pale yellow crystalline solid; m.p. 61°–67° C.

The crude material was dissolved in hot methanol (1500 mls) and the solution was filtered, then cooled in ice for 2 hours. The solid precipitate was filtered and washed with ice-cold methanol (1 l). The solid was dried in vacuo (0.5 ml) for 2 hours and airdried overnight. The yield of first crop of material, p.m. 66.3°–67.5° C. was 412.2 g.

The filtrate was concentrated to 800 mls, then cooled to −22° C. overnight. A second crop was filtered off and washed with ice-cold methanol (300 mls). After drying, the yield of second crop material, m.p. 66.8°–68° C., was 116.5 g.

The total yield was 528.7 g., 87%. GC analysis showed greater than 99% purity for each crop.

STEP 2. Preparation of
4-Cyclohexyl-α,α-dichloroacetophenone

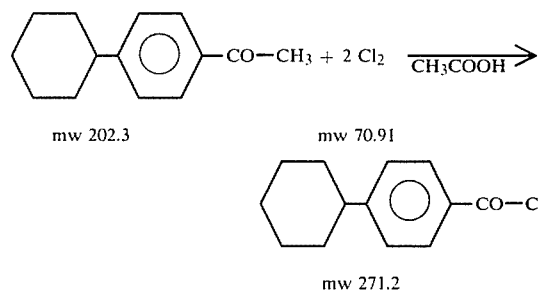

mw 202.3     mw 70.91 mw 271.2

Into a 3 liter round bottom flask equipped with a mechanical stirrer, gas inlet tube (below surface) and thermometer, was placed 4-cyclohexylaceptophenone (202.3 g, 1 mole) in glacial acetic acid (1300 mls). Stirring was begun and chlorine gas was introduced through the inlet tube.

When the reaction temperature climbed to 45° C., the outside of the flask was cooled as necessary with a stream of tap water and the temperature was controlled in this way between 40° and 45° C. for the remainder of the reaction. After 50 minutes, the solution became yellow at which time 150 grams of chlorine had been used. Chlorine addition was stopped (the solution remained yellow) and the reaction mixture was transferred to an Erlenmeyer flask (4 ls). As the solution cooled, the product began to crystallize out. Water (1300 ls) was added with stirring over 15 minutes while cooling the mixture in ice. The crystalline precipitate was stirred for 30 minutes in an ice bath, then filtered. The solid was washed with water (1 l), then suspended in water (2 ls) and filtered again. A further washing with water (4 ls) gave a white crystalline solid which was dried in vacuo to give the final product.

The total yield was 265.2 g, 98%, m.p. 92.5°–94° C. GC analysis showed greater than 99% purity.

STEP 3. The following three reactions may be carried out without isolation and purification of the intermediate products.

a. Preparation of
4-Cyclohexyl-α,α3-trichloroacetophenone mw 271.2     mw 70.91 mw 305.6

4-Cyclohexyl-α,α-dichloroacetophenone (623.7 g., 2.30 moles) was dissolved in methylene chloride (3120 mls) in a 5 liter round bottom flask equipped with a mechanical stirrer, submerged gas inlet tube, gas outlet through Dewar condenser with dry ice/acetone, and thermometer. To this solution was added iodine (29.2 g., 0.115 mole) and the mixture was stirred for 30 minutes. Chlorine gas (249.1 g., 3.51 moles) was then bubbled into the reaction mixture over a period of 1 hour and 15 minutes, maintaining a temperature of 20°–26° C. After stirring for 4 hours and 45 minutes (at which time the operator judged the reaction to be complete by the disappearance of signals at 6.70δ, 7.23δ, and 7.37δ and the appearance of signals at 6.73δ, 7.30δ, and 7.45δ in the 60 MC NMR spectrum) the mixture was poured into an ice cold solution of sodium bisulfite (145 g.) in water (1000 mls) with mechanical stirring while cooling in an ice bath. After stirring for 30 minutes, the layers were separated and the aqueous layer was extracted with methylene chloride (540 mls). The combined organic solution was washed with cold water 6 times (675 mls). The organic solution was then dried over anhydrous sodium sulfate, filtered, and the clear solution was concentrated in vacuo to 2875 mls, giving a 0.80 molar solution in methylene chloride which was used in the following reaction.

It is understood that the above chlorination step is not required where a 3-chloro substituent is not desired in the final product, or where a 3- substituent is already present.

b. Preparation of
4-Cyclohexyl-α-hydroxy-β,β,3-trichloroethylbenzene mw 305.6

NaBH₄  $\dfrac{\phi CH_2-N^+[(CH_2)_3-CH_3]_3Cl^-}{CH_2Cl_2, H_2O}$ ⟶ mw 37.82

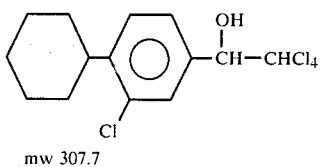

mw 307.7

4-Cyclohexyl-α,α,3-trichloroacetophenone (2360 mls of a 0.80 molar solution in methylene chloride from the previous reaction, 1.89 moles) was placed in a 6 liter Erlenmeyer flask and cooled in an ice bath. To this solution was added sodium borohydride (21.4 g., 0.566 mole). This mixture was stirred in an ice bath for 30 minutes. To this mixture was then added water (500 mls) followed by benzyl tri-n-butylammonium chloride (14.7 g., 0.047 mole). This mixture was stirred vigorously in an ice bath for 30 minutes. The layers was separated and the aqueous layer was extracted with methylene chloride twice (200 mls. each time). The combined organic solution was washed with 1% sulfuric acid solution (400 mls), water (400 mls), and saturated sodium chloride solution (400 mls). The organic solution was then dried over anhydrous sodium sulfate, filtered, and the methylene chloride filtrate was used in the following reaction.

c. Preparation of 4-Cyclohexyl-α-hydroxy-β,β,3-trichloroethylbenzene mesylate

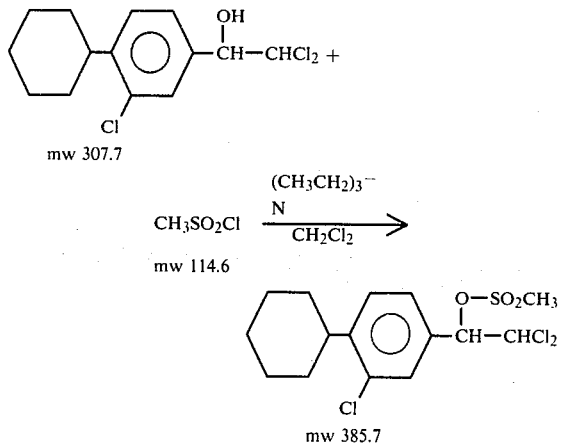

The methylene chloride solution from the previous reaction was transferred to a 5 liter round bottom flask equipped with a mechanical stirrer, thermometer, addition funnel, and drying tube. The solution was cooled to 0° C. and methanesulfonyl chlride (237.9 g., 2.08 moles) was added. With constant cooling and stirring, triethylamine (228.8 g., 2.27 moles) was added over a period of 1.5 hours maintaining the temperature below 5° C. The reaction mixture was stirred for an additional 1 hour. The mixture was washed twice with cold water (500 mls. each), cold 5% hydrochloric acid solution (500 mls.), cold 5% sodium bicarbonate solution (500 mls), and saturated sodium chloride solution (500 mls.). The methylene chloride solution was then dried over anhydrous sodium sulfate, filtered, and the filtrate was evaporated in vacuo at approximately 45° C. The resulting viscous oil was stirred with 2B ethanol (1200 mls) for 16 hours. The resulting solid was collected by filtration and washed with cold 2B ethanol to give 560 g. of white solid after drying in vacuo, (m.p. 101°–102° C., 77% yield). GC analysis showed greater than 99% purity.

STEP 4. Preparation of 4-Cyclohexyl-β,3-dichlorostyrene

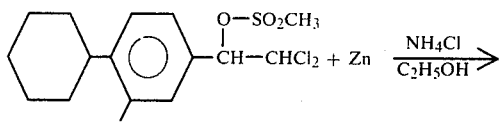

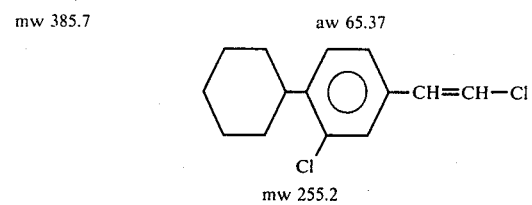

4-Cyclohexyl-α-hydroxy-β,β,3-trichloroethylbenzene mesylate (350.0 g., 0.907 mole) was suspended in 2B ethanol (1400 mls) in a 3 liter round bottom flask equipped with a mechanical stirrer and condenser. The suspension was heated to a slow reflux and ammonium chloride (53.49 g., 1.00 mole) was added. Zinc dust (118.6 g., 181 gram-atoms) was then added in four portions over a period of 20 minutes removing the heat source briefly during the additions to prevent excessive boiling. The reaction mixture was refluxed for 22.5 hours. The mixture was allowed to cool and the salts were removed by filtration. The filtrate was evaporated in vacuo and the residue was partitioned between ether (1400 mls) and 5% hydrochloric acid (1500 mls). The layers were separated and the organic layer was washed four times with water (1000 mls. each). The organic solution was dried over anhydrous sodium sulfate, filtered, and the filtrate was evaporated in vacuo to give a viscous oil (226.3 g., 98% yield) containing 62.7% of the trans isomer and 35.6% of the cis isomer of 4-cyclohexyl-β,3-dichlorostyrene as analyzed by gas chromatography.

STEP 5. Preparation of 3-Chloro-4-cyclohexyl-1-ethynylbenzene

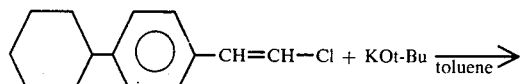

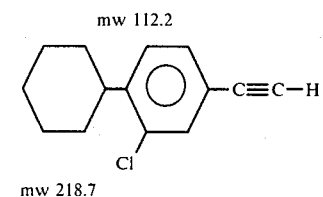

Potassium tert-butoxide (106.0 g., 0.944 mole) was suspended in toluene (1800 mls) in a 5 liter round bottom flask equipped with a mechanical stirrer, nitrogen inlet, condenser, and addition funnel. The suspension was heated to reflux under a nitrogen atmosphere. With the heat source removed, 4-cyclohexyl-β-3-dichlorostyrene (200.0 g., 0.784 mole) was added over a period of 15 minutes with vigorous stirring. During the addition the mixture thickened to a gel which thinned out near the end of the addition. The reaction mixture was stirred at reflux for 2.5 hours and then allowed to cool. The mixture was washed with 1.5% hydrochloric acid (1000 mls), 4 times with water (1000 mls each), and saturated sodium chloride solution (500 mls). The organic layer was dried over anhydrous sodium sulfate, filtered, and the filtrate was evaporated in vacuo at 45°–60° C. The residue was distilled in vacuo collecting a main fraction of 144.2 g. of the 3-chloro-4-cyclohexyl-1-ethynylbenzene (b. p. 87°–95° C./0.03 mls, 84% yield). GC analysis show greater than 99% purity.

EXAMPLE 2

By proceeding in accordance with Example 1, and substituting p-cyclohexylacetophenone by 3-methoxy-4-phenylacetophenone, there is obtained 3-methoxy-4-phenyl-1-ethynylbenzene, b.p. 133°–134° C./0.02 mm.

EXAMPLE 3

By proceeding in accordance with Example 1, and substituting p-cyclohexylacetophenone by 4-(2-chlorophenyl)acetophenone there is obtained the 4-(2-chlorophenyl)-1-ethynylbenzene, b.p. 101°–106° C./0.1 mm.

EXAMPLE 4

By proceeding in accordance with Example 1, and substituting p-cyclohexylacetophenone by 3-methyl-4-phenylacetophenone there is obtained 3-methyl-4-phenyl-1-ethynylbenzene, m.p. 57°–59° C.

EXAMPLE 5

By proceeding in accordance with Example 1, and substituting p-cyclohexylacetophenone by 3-chloro-4-phenylacetophenone there is obtained 3-chloro-4-phenyl-1-ethynylbenzene, b.p. 97°–100° C./0.09 mm.

EXAMPLE 6

By proceeding in accordance with Example 1 and substituting p-cyclohexylacetophenone by 3-fluoro-4-phenylacetophenone there is obtained 3-fluoro-4-phenyl-1-ethynylbenzene, b.p. 103° C./0.06 mm.

EXAMPLE 7

By proceeding in accordance with Example 1, and substituting p-cyclohexylacetophenone by 4-(2-fluorophenyl)acetophenone there is obtained 4-(2-fluorophenyl)-1-ethynylbenzene, b.p. 94°–97° C./0.2 mm.

EXAMPLE 8

By proceeding in accordance with Example 1, and substituting p-cyclohexylacetophenone by 4-(2,4-difluorophenyl)acetophenone there is obtained 4-(2,4-difluorophenyl)-1-ethynylbenzene, b.p. 95°–101° C./0.1 mm.

EXAMPLE 9

By proceeding in accordance with Example 1, and substituting p-cyclohexylacetophenone by 4-(2,6-difluorophenyl)acetophenone there is obtained 4-(2,6-difluorophenyl)-1-ethynylbenzene, m.p. 81°–83° C.

EXAMPLE 10

By proceeding in accordance with Example 1, and substituting p-cyclohexylacetophenone by 4-(o-tolyl)acetophenone there is obtained 4-(o-tolyl)-1-ethynylbenzene, b.p. 29°–30° C.

We claim:

1. Process for preparing an ethynylbenzene derivative of the general formula:

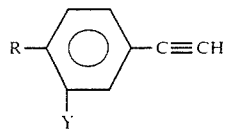

wherein
Y is hydrogen, halogen or loweralkyl of 1 to 3 carbon atoms;
R may stand for a ring of the structure:

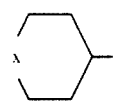

wherein x is 1 to 3, or a ring of the structure:

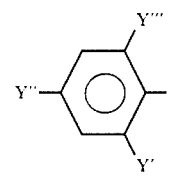

wherein
Y' is hydrogen, halogen, loweralkyl of 1–3 carbon atoms and loweralkoxy of 1–3 carbon atoms;
Y" is hydrogen or halogen; and
Y''' is hydrogen or halogen,
provided Y, Y', Y" and Y''' are not all hydrogen at the same time, which comprises reacting a benzyl alcohol of the general formula:

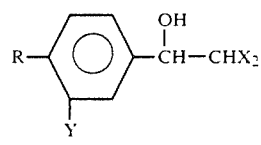

wherein R and Y are as previously defined and X is chloro or bromo, with a sulfonyl chloride of the formula: R'SO₃Cl wherein R' is alkyl, aryl or a loweralkyl substituted alkyl in the presence of a base, to form the corresponding sulfonyl derivative of the formula:

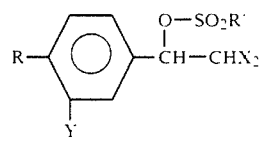

reducing said sulfonyl derivative of the formula in the presence of zinc to form the halostyrene of the formula:

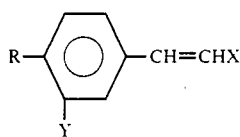

and then dehydrohalogenating said halostyrene compounds by reaction with an alkali metal alkoxide.

2. The process according to claim 1, characterized by the fact that R is cyclohexyl, Y is chloro, X is chloro, and R' is methyl, and the product obtained is 3-chloro-4-cyclohexyl-1-ethynylbenzene.

3. The process according to claim 1, characterized by the fact that R is phenyl, Y', Y" and Y''' are hydrogen, Y is methoxy, X is chloro and R' is methyl and the product obtained is 3-methoxy-4-phenyl-1-ethynylbenzene.

4. The process according to claim 1, characterized by the fact that R is phenyl, Y' is chloro, Y, Y" and Y''' are hydrogen, X is chloro and R' is methyl and the product obtained is 4-(2-chlorophenyl)-1-ethynylbenzene.

5. The process according to claim 1, characterized by the fact that R is phenyl, Y', Y" and Y''' are hydrogen, Y is methyl, X is chloro and R' is methyl and the product obtained is 3-methyl-4-phenyl-1-ethynylbenzene.

6. The process according to claim 1, characterized by the fact that R is phenyl, Y', Y" and Y''' are hydrogen, Y is chloro, X is chloro and R' is methyl and the product obtained is 3-chloro-4-phenyl-1-ethynylbenzene.

7. The process according to claim 1, characterized by the fact that R is phenyl, Y', Y" and Y''' are hydrogen, Y is fluoro, X is chloro and R' is methyl and the product obtained is 3-fluoro-4-phenyl-1-ethynylbenzene.

8. The process according to claim 1, characterized by the fact that R is phenyl, Y' is fluoro, Y" and Y''' are hydrogen, X is chloro and R' is methyl and the product obtained is 4-(2-fluorophenyl)-1-ethynylbenzene.

9. The process according to claim 1, characterized by the fact that R is phenyl, Y' and Y" are each fluoro, Y''' is hydrogen, X is chloro and R' is methyl and the product obtained is 4-(2,4-difluorophenyl)-1-ethynylbenzene.

10. The process according to claim 1, characterized by the fact that R is phenyl, Y' and Y''' are each fluoro, Y" is hydrogen, X is chloro and R' is methyl and the product obtained is 4-(2,6-difluorophenyl)-1-ethynylbenzene.

11. The process according to claim 1, characterized by the fact that R is phenyl, Y' is methyl, Y" and Y''' are hydrogen, X is chloro and R' is methyl and the product obtained is 4-(o-tolyl)-1-ethynylbenzene.

12. Process for preparing an ethynylbenzene derivative of the general formula:

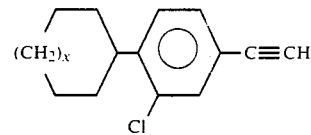

wherein:
x is 1 to 3, and
characterized by treating a dichloroacetophenone of the formula:

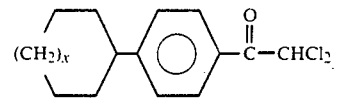

wherein x is as hereinbefore described, with chlorine to form the corresponding α,α-3-trichloro compound of the formula:

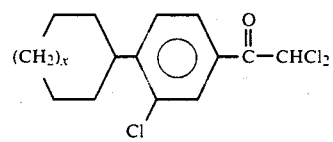

wherein x is as hereinbefore defined:
catalytically reducing the α,α3-trichloro compound to form the benzyl alcohol of the formula:

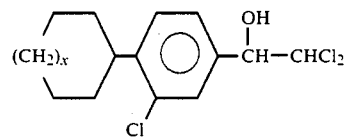

wherein x is as previously defined;
reacting the benzyl alcohol compound with a sulfonyl chloride of the formula: R'SO₂Cl wherein R' is is alkyl, aryl or a loweralkyl substituted alkyl, to form the corresponding sulfonyl derivative of the formula:

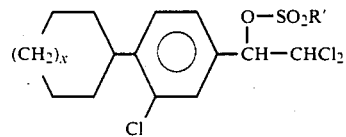

wherein x and R' are as hereinbefore defined,
reducing said sulfonyl derivative in the presence of zinc to form the chlorostyrene of the formula:

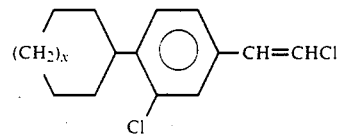

wherein x is hereinbefore defined, and then treating said chlorostyrene compounds with a strong base to form the desired ethynybenzene derivative.

* * * * *

UNITED STATES PATENT AND TRADEMARK OFFICE
CERTIFICATE OF CORRECTION

PATENT NO. : 4,267,388
DATED : May 12, 1981
INVENTOR(S) : Paul Darkes et al

It is certified that error appears in the above-identified patent and that said Letters Patent are hereby corrected as shown below:

Column 4, line 66, delete "$CH_3]_3Cl$" and insert

--$CH_3]_3CL^-$--

Column 6, line 67, delete "cyclohexyl-β-" and insert --cyclohexyl- β,--

Column 7, line 19 delete "0.02" and insert --0.2--

Signed and Sealed this

Eleventh Day of May 1982

[SEAL]

Attest:

GERALD J. MOSSINGHOFF

Attesting Officer      Commissioner of Patents and Trademarks